(12) United States Patent
Almau et al.

(10) Patent No.: US 7,879,568 B2
(45) Date of Patent: Feb. 1, 2011

(54) METHOD FOR THE DIAGNOSIS AND PROGNOSIS OF DEMYELINATING DISEASES

(75) Inventors: Carlos Matute Almau, Leioa-Vizcaya (ES); María Domercq García, Leioa-Vizcaya (ES); Alberto Pérez Samartín, Leioa-Vizcaya (ES); Fernando Pérez Cerdá, Leioa-Vizcaya (ES); Ainara Vallejo Illarramendi, Leioa-Vizcaya (ES); Estíbaliz Etxebarria Galnares, Leioa-Vizcaya (ES); Ormaetxea Olatz Pampliega, Leioa-Vizcaya (ES); Pablo Villoslada Díaz, Leioa-Vizcaya (ES); Alfredo Rodríguez-Antigüedad Zarranz, Leioa-Vizcaya (ES)

(73) Assignee: Universidad Del Pais Vasco (ES)

( * ) Notice: Subject to any disclaimer, the term of this patent is extended or adjusted under 35 U.S.C. 154(b) by 316 days.

(21) Appl. No.: 11/915,324

(22) PCT Filed: May 22, 2006

(86) PCT No.: PCT/ES2006/000269

§ 371 (c)(1),
(2), (4) Date: Mar. 11, 2008

(87) PCT Pub. No.: WO2006/125838

PCT Pub. Date: Nov. 30, 2006

(65) Prior Publication Data

US 2008/0200384 A1    Aug. 21, 2008

(30) Foreign Application Priority Data

May 23, 2005   (ES)  ............ 200501248

(51) Int. Cl.
*G01N 33/567* (2006.01)
*G01N 33/53* (2006.01)
*C12Q 1/68* (2006.01)

(52) U.S. Cl. ............... 435/7.21; 435/6

(58) Field of Classification Search .......... None
See application file for complete search history.

(56) References Cited

FOREIGN PATENT DOCUMENTS

EP    0 454 026 A1    10/1991
WO    2005041978 A1    5/2005

OTHER PUBLICATIONS

Mazumder et al., 2003. Trends in Biochemical Sciences 28:91-98.*
Ohgoh et al. 2002 (Journal of Neuroimmunology 125:170-178.*
Heid 1996 (Genome Research 6:986-994).*
Vallejo-Illarramendi 2006 Neurobiology of Disease 21:154-164.*
Pitt 2003. Neurology 61:1113-1120.*
Figiel, Maciej, et al., "Regulation of glial glutamate transporter expression by growth factors", "Experimental Neurology", 2003, pp. 124-135, vol. 183.
Fosse, V. M., et al., "A bioluminescence method for the measurement of L-glutamate: . . . (Abstract Only)", "J. Neurochem.", 1986, pp. 340-349, vol. 47, No. 2.
Matute, Carlos, et al., "The link between excitotoxic oligodendroglial death and demyelinating diseases", "Trends in Neurosciences", Apr. 2001, pp. 224-230, vol. 24, No. 4.
Matute, Carlos, et al., "Multiple sclerosis: novel perspectives on newly forming lesions", "Trends in Neurosciences", Apr. 2005, pp. 173-175, vol. 28, No. 4.

* cited by examiner

*Primary Examiner*—Daniel E Kolker
(74) *Attorney, Agent, or Firm*—Steven J. Hultquist; Intellectual Property/Technology Law

(57) ABSTRACT

The present invention refers to the use of glutamate transporters, glutamate and EGF to detect the presence of demyelinating diseases in a subject, to determine the status or severity of the same or to monitor the effects of a therapy administered to a subject who suffers from such diseases; to the use of the said markers for the searching, identification, development and evaluation of the efficacy of compounds for the treatment of such diseases, with a view to developing new drugs; to the use of compounds which promote the expression of the EAAT1 and EAAT2 transporters, as well as EGF for the treatment of demyelinating diseases. In a preferred embodiment, the methods and compounds of the invention are applicable to MS.

11 Claims, 9 Drawing Sheets

METHOD FOR THE DIAGNOSIS AND PROGNOSIS OF DEMYELINATING DISEASES

CROSS-REFERENCE TO RELATED APPLICATIONS

This application is filed under the provisions of 35 U.S.C. §371 and claims the priority of International Patent Application No. PCT/ES2006/000269 filed May 22, 2006, and the priority of Spanish Patent Application No. P200501248 filed May 23, 2005. The disclosures of said international patent application and Spanish patent application are incorporated herein by reference, in their entireties, for all purposes.

FIELD OF THE INVENTION

The present invention relates to the field of demyelinating diseases, preferably multiple sclerosis and to the use of glutamate transporters as markers of said diseases and to the use of substances which enhance the expression of said transporters for the treatment of the aforementioned diseases.

BACKGROUND OF THE INVENTION

Multiple sclerosis (MS) is the most frequently occurring demyelinating disease of the central nervous system (CNS). It affects 1.5 million people worldwide and its symptoms generally appear in young adults, with the result that it has very serious consequences at both personal and socioeconomic levels.

It is thought that MS susceptibility is due to unknown genetic and environmental factors. The prevalence of the disease is around 50 to 100 people per 100,000 inhabitants in the high risk regions, which are located principally in the septentrional zones of the northern hemisphere, in Europe and America. The risk of having MS increases 10 to 20 times in first degree family relatives and the concordance between monozygotic twins (genetically identical) rises up to 30-35%, whereas dizygotic twins only reach a concordance of 2-5%. Genetic susceptibility has not yet been characterized. To date, there is evidence that it may reside in some polymorphism of genes encoding human leukocyte antigens (HLA), myelin oligodendrocyte glycoprotein (MOG), and other genes on chromosomes 10 and 15.

There is a general consensus among the EM researches that the disease has two phases; an inflammatory primary phase, autoimmune in nature, and other neurodegenerative progressive secondary phase. The primary phase begins with the activation of myelin-specific T cells which pass through the blood brain barrier. Once inside the central nervous system (CNS), they release proinflammatory cytokines, unleashing an immunological cascade which leads to myelin destruction and oligodendrocyte death, in part reversible after the inflammatory event. A more precise knowledge of the autoimmune process has helped to develop immunomodulatory agents whose therapeutic efficacy is quite modest. However, drugs delaying or impeding the advance of the neurodegenerative phase of the disease which is accompanied by progressive neurological deterioration and invalidity and characterized by the appearance of permanent and serious demyelinating lesions in the white matter, with massive loss of oligodendrocytes, atrophy and severe axonal damage have not yet been developed.

To date, various therapeutic targets have been described for use during the inflammatory phase of MS (Zamvil and Steinman, 2003, Neuron 38, 685-688). Among them can be found those aimed to reduce CNS inflammation initiated by the activation of myelin-specific T cells, which penetrate into CNS tissue and release proinflammatory cytokines such as interferon gamma and tumor necrosis factor alpha (TNFα). In this sense, the interferon beta immunomodulator, approved for the treatment of relapsing-remitting MS, prevents cellular interactions which lead to the penetration of activated T cells via the vascular endothelium. Other treatments in clinical assay phase are aimed to neutralize the activity of proinflammatory cytokines and/or to enhance the anti-inflammatory ones. A recent study which employed an animal model of MS, the experimental autoimmune encephalitis (EAE; Youssef et al., 2002, nature 420, 78-84), has shown that the drug atorvastatin which is used for the treatment of hypercholesterolemia, is also a potent immunomodulator which can prevent or revert chronic EAE via the enhancement of the secretion of anti-inflammatory cytokines and the inhibition of the production of proinflammatory cytokines. However, there is no therapeutic target for intervention during the progressive secondary phase, which is most related to the irreversible degeneration of the CNS of the patient.

An important finding in recent years which has contributed to the understanding of the MS etiology, has been the discovery of the sensitivity of oligodendrocytes to glutamate (Matute et al., 2001, TINS 24, 224-230). Thus, stimulation of glutamate receptors of the α-amino-3-hydroxy-5-methyl-4-isoxazolpropionic acid (AMPA) and kainate subtypes in oligodendrocytes induces the death thereof, a phenomenon known as oligodendroglial excitotoxicity (Matute et al., 1997, Proc Natl Acad Sci USA 94, 8830-8835; McDonald et al., 1998, Nat Med 4, 291-297). Moreover, the in vivo application to animals of agonists of the said receptors provokes atrophy of the optic nerve associated with massive demyelination, which is reminiscent of that which is found in MS (Matute, 1998, Proc. Natl. Acad. Sci USA 95, 10229-10234). The hypothesis of the implication of oligodendroglial excitotoxicity in MS has been subsequently substantiated following the finding that antagonists of AMPA and kainate receptors reduce the severity and prevent the appearance of episodes in animals with EAE (Smith et al., 2000, Nat Med 6, 62-66; Pitt et al., 2000, Nat Med 6, 67-70). These studies indicate that as a consequence of the immune reaction in EAE, an alteration in the homeostasis of glutamate is produced which leads to the overactivation of glutamate receptors and oligodendroglial death.

Like in EAE, the glutamate homeostasis is altered in MS, corroborating the glutamatergic hypothesis of MS. Thus, glutamate levels are elevated in cerebrospinal fluid in patients with acute MS (Stover et al., 1997, Eur J. Clin Invest 27, 1038-1043) and with progressive secondary MS (Sarchielli et al, 2003, Arch Neurol 60, 1082-1088), as well as in blood serum before the beginning of the episode (Westall et al, 1980, J Neurol Sci 47, 353-364). In addition, the expression of the enzymes glutamine synthetase and glutamate dehydrogenase which are responsible for the degradation of glutamate, is reduced while the enzyme glutaminase, which produces glutamate is elevated in the white matter of patients with MS (Werner et al, 2001, Ann Neurol 50, 169-180), suggesting an alteration in the levels of said neurotransmitter. However, little is known about the expression and function of glutamate transporters in MS.

Glutamate transporters (EAATs) are responsible for the maintenance of low extracellular levels of said amino acid, and particularly, in the synapse, which permits the maintenance of an adequate signal/noise ratio and avoids overactivation of glutamatergic receptors and cell death (Danbolt, 2001, Prog Neurobiol 65, 1-105). To date, five subtypes of EAATs have been cloned (Arriza et al., 1994, Proc Natl Acad Sci USA 94, 4155-4160; Danbolt, 2001, Prog Neurobiol 65, 1-105). The EAAT1 and EAAT2 subtypes (and their rat homologs GLAST and GLT-1) are expressed principally in cells of glial origin, EAAT3 (and its rat homologue EAAC1) and EAAT4 are expressed in neurons, and EAAT5 is located exclusively in the retina. Glutamate transporters have been found to be widely distributed in the brain and spinal cord (Danbolt, 2001, Prog. Neurobiol 65, 1-105), as well as in white matter tracts such as the optic nerve (Domercq et al. 1999, Eur J Neurosci 11, 2226-2236). Extracellular glutamate uptake takes place principally via glial transporters and blockade of these leads to processes of chronic neurodegeneration as a result of the increase in the extracellular concentration of glutamate (Rothstein et al., 1996, Neuron 16: 675-686). In fact, mice deficient in the GLT-1 transporter develop lethal spontaneous epileptic activity and present larger susceptibility to acute cortical damage (Tanaka et al, 1997, Science 276, 1699-1702). Given this essential role of EAAT1/GLAST and EAAT2/GLT-1, it is likely that an alteration in their expression and/or function may contribute to the increased glutamate levels which have been found in some CNS pathologies, such as demyelinating diseases.

SUMMARY OF THE INVENTION

The principal objective of the present invention is to provide an in vitro method to detect the presence of demyelinating diseases, including MS in particular, to determine the prognosis of the same and to monitor the effect of treatments used for these diseases. An additional objective consists of provide a series of compounds for the treatment of demyelinating diseases, including MS in particular.

The present invention is based on the discovery that the inhibition of the activity of glutamate transporters produces oligodendroglial death in vitro and neurological damage in vivo as demyelination and axonal damage, which are characteristic of the neurodegenerative phase of MS; on the discovery that the expression of said transporters is regulated by the levels of glutamate; and on the discovery that the levels of glutamate and the expression levels of EAAT1 and EAAT2 transporters are increased in blood samples as well as in samples of post-mortem optic nerve from MS patients with respect to controls who are unaffected by MS, constituting said overexpression a compensatory mechanism in response to the increased levels of glutamate and produced by epidermal growth factor (EGF), a positive modulator of the EAAT1 and EAAT2 transcription.

Thus, the invention relates in general to the use of the EAAT1 and EAAT2 transporters, of the glutamate and/or of the EGF modulator as markers of demyelinating diseases and in particular of MS, as well as methods and kits for putting into practice the present invention.

In an aspect, the invention relates to an in vitro method to detect a demyelinating disease in a subject, or to determine the status or severity of said disease in a subject, or to monitor the effect of the therapy administered to a subject who presents said disease, comprising the use of EAAT1 and EAAT2, of glutamate and/or of the EGF modulator as markers of demyelinating diseases.

In a further aspect, the invention relates to the use of a nucleotide sequence of a gene selected from the EAAT1 gene, the EAAT2 gene and the EGF gene, or of a peptide sequence of a protein selected from the EAAT1, EAAT2 and EGF, or of an antibody with the capacity to bind to a protein selected from EAAT1, EAAT2 and EGF or to fragments thereof containing antigenic determinants, or of the glutamate dehydrogenase enzyme, for detecting in vitro the presence of a demyelinating disease in a subject, or for determining in vitro the status or severity of said demyelinating disease, or for determining in vitro the effect of the treatment of a subject who presents a demyelinating disease.

In another aspect, the invention relates to a method for the screening, searching, identification, development and evaluation of the efficacy of compounds for the treatment of demyelinating diseases, based on the quantification of a gene selected from EAAT1, EAAT2 and EGF genes and any combination thereof, or on the quantification of the levels of glutamate.

In another aspect, the invention relates to the use of (i) a nucleotide sequence of a gene selected from the EAAT1, EAAT2 and EGF genes, or of (ii) an amino acid sequence of a protein selected from EAAT1, EAAT2 and EGF or of (iii) an antibody which has a capacity to bind to a protein selected from EAAT1, EAAT2 and EGF or to fragments thereof containing antigenic determinants, in a method of screening, searching, identification, development and evaluation of the efficacy of compounds for the treatment of demyelinating diseases.

In another aspect, the invention relates to an in vitro method for the identification and evaluation of the efficacy of treatments for demyelinating diseases comprising the quantification of the levels of glutamate, or the quantification of the EAAT1, EAAT2 and/or EGF proteins levels, or the quantification of the expression levels of the EAAT1, EAAT2 and/or EGF genes in a given subject during the distinct phases or stages of the disease, or during periods of treatment and periods of non-treatment, and its comparison with normal control values or with previous values from the same patient.

In another aspect, the invention relates to a pharmaceutical composition comprising an effective therapeutic quantity of a compound which blocks the inhibition of the expression or the activity of a glutamate transporter selected from the EAAT1 and EAAT2 transporters, or of a compound which promotes or enhances the expression of said EAAT1 and/or EAAT2 transporters, or of a compound which reduces the level of glutamate, together with one or more excipients and/or vehicles pharmaceutically acceptable. In a particular embodiment, said pharmaceutical composition comprises a positive modulator of the expression of the EAAT1 and EAAT2 transporters, such as EGF.

In another aspect, the invention relates to the use of a compound which blocks the inhibition of the expression or the activity of a glutamate transporter selected from EAAT1 and EAAT2 transporters, or of a compound which promotes or enhances the expression of said transporters, or of a compound which reduces the level of glutamate, in the manufacture of a pharmaceutical composition for the treatment of demyelinating diseases.

In another aspect, the invention relates to a kit, such as a kit suitable for the detection of a demyelinating disease in a subject or for the determination of the status or severity of said disease in a subject, or to monitor the effect of the therapy administered to a subject who presents with said disease.

DETAILED DESCRIPTION OF THE INVENTION

Figure 1:
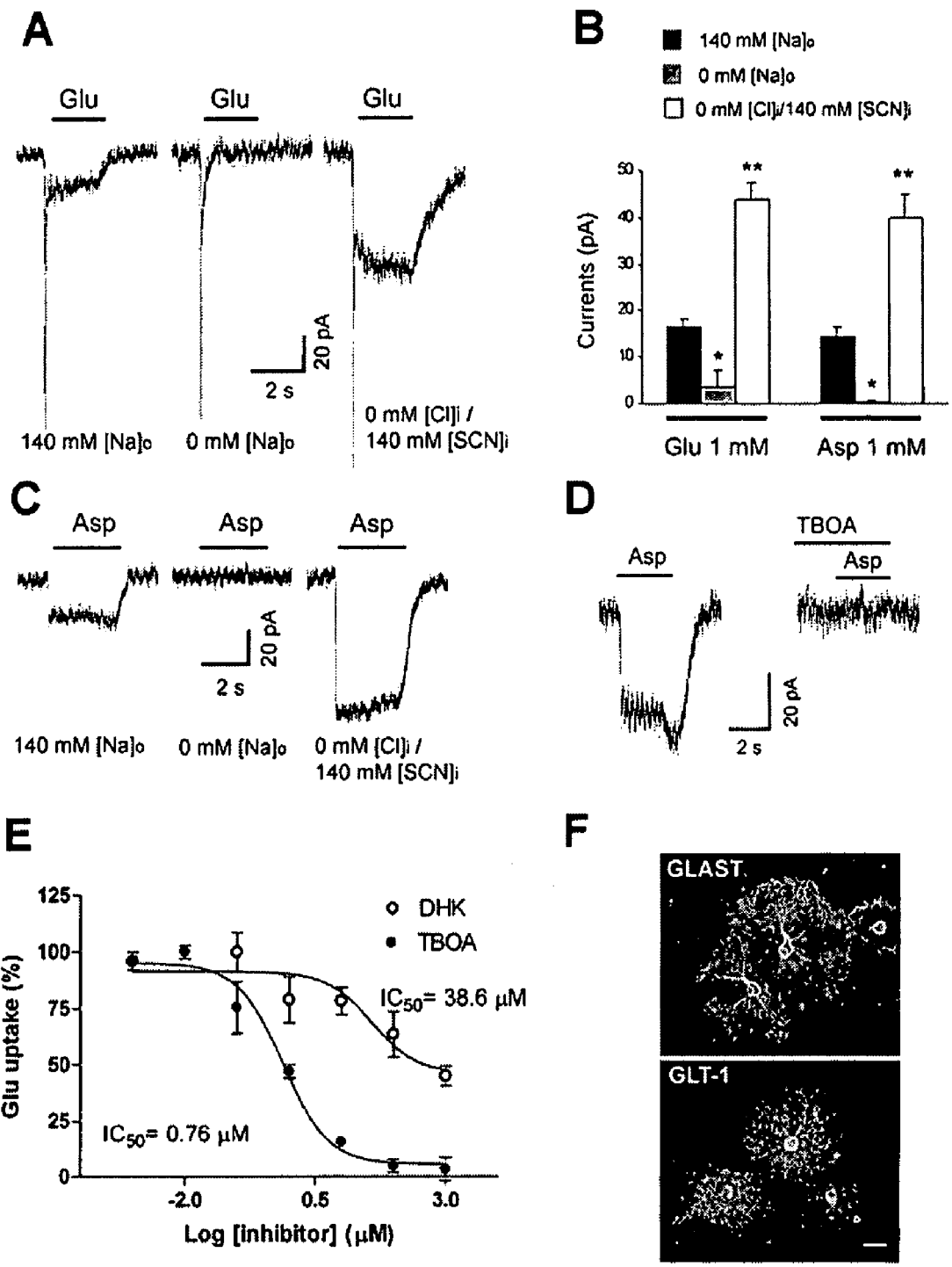
FIG. 1 shows the electrophysiological properties of glutamate transporters in oligodendrocytes in culture. The application of glutamate and aspartate produces a slow, non-desensitizing current, which is inhibited by substituting extracellular $Na^+$ for $Li^+$ and by the presence of TBOA inhibitor, and enhanced in the presence of $SCN^-$ ions at intracellular level. The pharmacological characteristics indicate the expression of the EAAT1/GLAST and EAAT2/GLT-1 subtypes.

In order to facilitate the understanding of the invention which is the object of the present patent application, it is expounded the meaning of some terms and expressions in the context of the present invention:

The term "subject" refers to a member of a species of a mammalian animal, including but not being limited to domestic animals, primates and humans; the subject is preferably a human being, male or female, of any age or race.

The term "demyelinating diseases" refers to those diseases in which the pathogenic process induces the destruction of myelin, which is the lipoprotein layer covering nerves and facilitating transmission of impulses through nerve fibers; non-limiting illustrative examples of demyelinating diseases include: multiple sclerosis (MS), Devic's syndrome, Baló's disease, Marchiafava-Bignami disease, central pontine myelinolysis, disseminated acute encephalomyelitis and acute necrotizing hemorrhaging encephalomyelitis.

The term "protein" refers to a molecular chain of amino acids, jointed by covalent or non-covalent bonds. The term includes all forms of post-translational modifications, e.g. glycosylation, phosphorylation or acetylation.

The term "antibody" refers to a protein with a capacity to specifically bind to "antigen". The term "antibody" comprises monoclonal antibodies or polyclonal antibodies, which are intact, or fragments thereof which retain the capacity to bind to an antigen, recombinant antibodies, combibodies, etc, which can be human or humanized as well as of non-human origin.

The term "oligonucleotide primer", as used in the present invention, refers to a nucleotide sequence which is complementary to a nucleotide sequence of a gene selected from the gene encoding the subtype 1 glutamate transporter (EAAT1) [EAAT1 gene], the gene encoding the subtype 2 glutamate transporter (EAAT2) [EAAT2 gene] and the gene encoding epidermal growth factor (EGF) [EGF gene]. Each primer hybridizes with its target nucleotide sequence and acts as an initiation site for DNA polymerization.

The present invention is based on the discovery that the expression level of the EAAT1 and/or EAAT2 genes, as well as the expression level of their corresponding proteins, is increased in MS patients with respect to control subjects; on the discovery that glutamate levels in MS patients are elevated with respect to control subjects; and on the discovery that the expression of the gene encoding EGF, a positive modulator of the transporters promoter, as well as the corresponding protein, are elevated in MS patients with respect to control subjects.

As a consequence, the evaluation and comparison of the expression levels of the EAAT1 and/or EAAT2 genes, as well as the corresponding proteins, and/or the evaluation and comparison of the level of the gene encoding EGF, as well as the level of the corresponding protein, and/or the evaluation and comparison of the glutamate levels in a biological sample from a subject can be used for the diagnosis or prognosis of demyelinating diseases in general and, of MS in particular. As illustrative way, elevated levels of said markers with respect to levels from control subjects (i.e. subjects without a clinical history of demyelinating diseases and/or who do not show demyelinating diseases, e.g. MS) or with respect to normal reference values (obtained, in general, from control subjects) is indicative of a demyelinating disease, or of a higher risk or predisposition of the subject to develop said disease. Comparison of the levels of said markers, at a given moment, in a subject diagnosed or not with a demyelinating disease, with those of previous samples from the same subject may be indicative of the evolution and prognosis of said demyelinating disease or of the predisposition of the subject to develop said disease.

The previously mentioned finding may be used, among other applications, in assays of diagnosis or of evaluation of risk or predisposition of a subject to develop a demyelinating disease, in prognosis assays, in assays which monitor the effect of the therapy administered to a subject in order to analyze the efficacy of the therapy and the evolution of the disease, and in screening assays of compounds potentially useful for the treatment of demyelinating diseases.

The invention provides, as a result, methods to detect and quantify the expression of the EAAT1 and EAAT2 genes and the gene encoding EGF, and of the corresponding proteins, as well as methods to detect and quantify glutamate levels in a biological sample. The invention also provides methods to detect interactions among said products and other compounds, e.g., antagonists.

In one aspect, the invention relates to an in vitro method to detect a demyelinating disease in a subject, or to determine the status or severity of said disease in a subject, or to monitor the effect of the therapy administered to a subject who presents said disease, hereinafter the method of the invention, comprising:

a) quantifying the level of expression of a gene in a sample from said subject, wherein said gene is selected from the gene encoding the subtype 1 glutamate transporter (EAAT1) [EAAT1 gene], the gene encoding the subtype 2 glutamate transporter (EAAT2) [EAAT2 gene] and the gene encoding the epidermal growth factor (EGF) [EGF gene], or any combination thereof; and b) comparing said level with that from a control sample;

wherein an increase in said level with respect to that in the control sample indicates the presence of a demyelinating disease;

or alternatively, a) quantifying the protein level in a sample from said subject, wherein said protein is selected from the subtype 1 glutamate transporter (EAAT1), the subtype 2 glutamate transporter (EAAT2) and epidermal growth factor (EGF), and any combination thereof; and b) comparing said level with that of a control sample;

wherein an increase in said level with respect to the level in a control sample indicates the presence of a demyelinating disease;

or, alternatively, a) quantifying the level of glutamate in a test sample from said subject; and b) comparing said level with that from a control sample;

wherein an increase in said level with respect to the level in a control sample indicates the presence of a demyelinating disease.

The method provided by this invention presents high sensitivity and specificity and is based on the fact that subjects diagnosed with a demyelinating disease, mainly MS, show high levels of glutamate and of mRNA encoding the EAAT1, EAAT2 and/or EGF genes and/or elevated concentrations of the EAAT1, EAAT2 and/or EGF proteins in comparison to those found in samples from control subjects, who have no clinical history of a demyelinating disease.

In order to put into practice the method of the invention, a biological sample from the subject to be studied is obtained. Non-limiting illustrative examples of said samples include distinct types of biological fluids, such as blood, cerebrospinal fluid, peritoneal liquid, excrement, urine and saliva, as well as tissue samples. Samples of biological fluids and tissues can be obtained via any conventional method; As illustrative way, said tissue samples can be samples from biopsies obtained by surgical resection. The samples can be obtained from subjects previously diagnosed with a demyelinating disease (patients), e.g. MS, or non-diagnosed subjects, or patients who are undergoing treatment for a demyelinating disease, e.g. MS, or patients who have previously been treated for the same.

In a particular embodiment, the method of the invention comprises quantifying the expression level of a gene selected from the EAAT1 gene, the EAAT2 gene and the EGF gene, and any combination thereof, in a sample from said subject and its comparison with the corresponding expression level in a control sample, wherein an increase in said level with respect to the level in the control sample is indicative of a demyelinating disease, e.g. MS. The method of the invention includes the possibility of quantifying not only the level of only one of said genes, but the possibility of quantifying the levels of two or even three of said genes.

The expression level of a gene can be quantified by quantifying the level of mRNA encoding said gene, or alternatively, the level of complementary DNA (cDNA) to said gene mRNA. In this case, the method of the invention includes an extraction step to obtain total RNA, which can be performed by means of conventional techniques (Chomczynski et al., Anal. Biochem., 1987, 162: 156; Chomczynski P., Biotechniques, 1993, 15:532).

Practically any conventional method can be used within the framework of the invention to detect and quantify the mRNA levels encoding EAAT1, EAAT2 and/or EGF or their corresponding cDNA. By way of non-limiting example, the mRNA levels encoding said genes can be quantified by means of employing conventional methods, for example, methods comprising mRNA amplification and the quantification of the product of said mRNA, such as electrophoresis and staining, or alternatively, by means of Southern blot together with suitable probes, Northern blot together with specific probes for the mRNA of the relevant gene (EAAT1, EAAT2 or EGF) or of their corresponding cDNA, mapping with S1 nuclease, RT-LCR, hybridization, microarrays, etc., preferably by means of real time quantitative PCR using a suitable marker (see the Example which accompanies this description). Similarly, the levels of cDNA corresponding to said mRNA encoding EAAT1, EAAT2 and/or EGF can also be quantified using conventional techniques; in this case, the method of the invention includes a synthesis step of the corresponding cDNA by means of reverse transcription (RT) of the corresponding mRNA followed by amplification and quantification of the amplification product of said cDNA; in a particular embodiment, the amplification is carried out qualitatively or quantitatively via PCR, using oligonucleotide primers which specifically amplify regions of the EAAT1, EAAT2 or EGF genes.

In another particular embodiment, the method of the invention comprises quantifying the level of a protein selected from the EAAT1, EAAT2 and EGF proteins, and any combination thereof, in a sample from said subject and its comparison with that of a control sample, wherein an increment in said level with respect to that of the control sample is indicative of a demyelinating disease, e.g. MS. The method of the invention includes the possibility of quantifying not only the level of one of said proteins, but the possibility of quantifying the levels of two or even three of said proteins.

The level (concentration) of said EAAT1, EAAT2 and/or EGF proteins can be quantified by means of any conventional method which permits the detection and quantification of said proteins in a sample from the subject. In this case, the method of the invention includes carrying out an extraction step in order to obtain a protein extract which contains said proteins, which can be performed using conventional techniques (Chomczynski et al., Anal. Biochem., 1987, 162: 156; Chomczynski P., Biotechniques, 1993, 15:532).

Practically any conventional method can be used within the context of the invention to detect and quantify the levels of EAAT1, EAAT2 and/or EGF. By way of non-limiting example, the levels of said proteins can be quantified by means of conventional methods, for example, using antibodies with a capacity to specifically bind to EAAT1, EAAT2 or EGF (or to fragments thereof containing antigenic determinants) and subsequent quantification of the resulting antibody-antigen complexes. The antibodies to be employed in these assays can be labeled or not. Illustrative, but non-exclusive examples of markers which can be used include radioactive isotopes, enzymes, fluorophores, chemiluminescent reagents, enzymatic substrates or cofactors, enzymatic inhibitors, particles, colorants, etc. There are a wide variety of well-known assays that can be used in the present invention, which use non-labeled antibodies (primary antibody) and labeled antibodies (secondary antibodies); among these techniques are included Western-blot or Western transfer, ELISA (enzyme linked immunosorbent assay), RIA (radioimmunoassay), competitive EIA (enzymatic immunoassay), DAS-ELISA (double antibody sandwich ELISA), immunocytochemical and immunohistochemical techniques, techniques based on the use of biochips or protein microarrays including specific antibodies or assays based on colloidal precipitation in formats such as dipsticks. Other ways of detecting and quantifying the EAAT1, EAAT2 or EGF proteins include techniques of affinity chromatography, binding-ligand assays, etc.

In a particular embodiment, the quantification of the levels of EAAT1, EAAT2 and/or EGF proteins is carried out using antibodies with a capacity to bind to EAAT1, EAAT2 or EGF (or fragments thereof which contain antigenic determinants) and subsequent quantification of the resulting complexes, for example, using immunochemical techniques which permit the quantification of antigen-antibody binding, for example Western Blot, ELISA, protein biochips, etc.; preferably, the quantification of the EAAT1, EAAT2 and/or EGF levels is performed by means of Western blot using appropriate antibodies capable of binding to said proteins [there are commercially available antibodies with a capacity to bind to said proteins (see the Example which accompanies this description)].

The functional nature of the EAAT1 and EAAT2 transporters can be determined by means of conventional methods, e.g. glutamate uptake assays in glial membrane vesicular preparations (see the Example which accompanies this description).

In another particular embodiment, the method of the invention comprises quantification of the glutamate level in a sample from said subject and its comparison with that from a control sample, wherein an increase in said level with respect to the level in the control sample is indicative of a demyelinating disease.

The level (concentration) of glutamate can be quantified by any conventional method which permits the detection and quantification of said compound in a sample from a subject. Preferably, the level of glutamate is determined in a blood, plasma or serum sample from a subject. Preferably, the glutamate level is determined in a blood sample, plasma or serum from the subject, thus, in this case, the method of the invention can include a previous treatment to separate plasma or serum, which can be carried out by conventional techniques.

Practically any conventional method can be used within the context of this invention to detect and quantify the glutamate level. By way of non-limiting example, the level of said compound can be quantified by means of enzymatic methods, e.g. by means of an enzymatic reaction using the glutamate dehydrogenase enzyme (see the Example which accompanies this description).

The method of the invention also comprises the step of comparing the expression levels of EAAT1, EAAT2 and/or EGF genes (obtained, for example, by quantifying the levels of mRNA corresponding to said genes, or of their cDNA), or of the level of the EAAT1, EAAT2 and/or EGF proteins, or of the glutamate level, determined in the sample from a subject who is the object of the study, with the levels of a control sample (i.e. with reference values). The expression levels of the EAAT1, EAAT2 and/or EGF genes, as well as those of the EAAT1, EAAT2 and/or EGF proteins, or of glutamate, can be determined by the previously mentioned techniques in samples from subjects who do not present demyelinating diseases, or who have no clinical history of demyelinating diseases. An increase in the expression levels of the EAAT1, EAAT2 and/or EGF genes, or of the EAAT1, EAAT2 and/or EGF proteins levels, or of glutamate level in the sample from the subject who is being studied, with respect to the corresponding levels in the control sample is indicative of a demyelinating disease, e.g. MS.

The nucleotide sequences of the EAAT1, EAAT2 and EGF genes, as well as the amino acid (peptide) sequences of said proteins and antibodies with a capacity to bind to said proteins, or fragments thereof containing specific antigenic determinants of said proteins, can be used for the in vitro detection (diagnosis) of a demyelinating disease in a subject, or for the in vitro determination of the status or severity of said demyelinating disease, or for the in vitro determination of the effect of treatment in a subject who presents a demyelinating disease.

Thus, in one aspect, the invention relates to the use of a nucleotide sequence of a gene for the in vitro detection (diagnosis) of a demyelinating disease in a subject, or for the in vitro determination of the status or severity of said demyelinating disease, or for the in vitro determination of the effect of treatment in a subject who presents a demyelinating disease, wherein said gene is selected from the EAAT1 gene, the EAAT2 gene and the EGF gene. In a particular embodiment, said disease is MS. Said nucleotide sequence can be a probe which is complementary to a nucleotide sequence present in said EAAT1, EAAT2 or EGF genes, useful to detect said nucleotide sequence of said genes.

In another aspect, the invention relates to the use of a peptide sequence of a protein for the in vitro detection (diagnosis) of a demyelinating disease in a subject, or for the in vitro determination of the status or severity of said demyelinating disease, or for the in vitro determination of the effect of treatment in a subject who presents a demyelinating disease, wherein said protein is selected from the EAAT1, EAAT2 and EGF proteins. In a particular embodiment, said disease is MS. Said peptide sequence can be a sequence comprising a epitope of said EAAT1, EAAT2 or EGF proteins.

In another aspect, the invention relates to the use of an antibody for the in vitro detection of a demyelinating disease in a subject, or for the in vitro determination of the status or severity of said demyelinating disease, or for the in vitro determination of the effect of treatment in a subject who presents a demyelinating disease, wherein said antibody is an antibody with a capacity to bind to a protein selected from EAAT1, EAAT2 and EGF or to fragments thereof containing antigenic determinants of said proteins. Said antibodies can be recombinant antibodies, monoclonal or polyclonal antibodies, intact, or fragments thereof which retain the capacity to bind to said proteins (EAAT1, EAAT2 or EGF), for example, $F_{ab}$, scFv (single-chain variable fragment) fragments, etc. and human, humanized or non-human origin antibodies. In a particular embodiment, said demyelinating disease is MS.

In another aspect, the invention relates to the use of the glutamate dehydrogenase enzyme for the in vitro detection (diagnosis) of a demyelinating disease in a subject, or for the in vitro determination of the status or severity of said demyelinating disease, or for the in vitro determination of the effect of a treatment in a subject who presents a demyelinating disease. In a particular embodiment, the demyelinating disease is MS.

Said nucleotide sequence of a gene selected from the EAAT1, EAAT2 and EGF genes, as well as said amino acid sequence of a protein selected from EAAT1, EAAT2 and EGF and said antibody with a capacity to bind to a protein selected from EAAT1, EAAT2 and EGF (or to fragments thereof, containing antigenic determinants), can be used for the screening, searching, identification, development and evaluation of the efficacy of compounds for the treatment of demyelinating disease, e.g. MS.

Thus, in another aspect, the invention relates to a method for the screening, searching, identification, development and evaluation of the efficacy of compounds for the treatment of demyelinating diseases comprising (i) putting into contact a cell system expressing a gene with a compound to be assayed and (ii) evaluating the expression of said gene(s), such that if said gene is overexpressed, the assayed compound is a compound potentially useful for the treatment of demyelinating diseases, wherein said gene is selected from the EAAT1, EAAT2, EGF genes and any combination thereof. Said cell system can be practically any cell system (e.g. a single cell) which expresses naturally or by recombination a gene selected from the EAAT1, EAAT2, EGF genes and any combination thereof. The expression of these genes can be evaluated by any conventional method, for example, by means of the quantification of mRNA expressing said genes or their corresponding cDNAs, or by means of the quantification of said EAAT1, EAAT2 or EGF proteins by any of the previously mentioned methods. When a compound increase the expression of EAAT1, EAAT2 or EGF, said compound becomes a potentially useful candidate for the treatment of demyelinating diseases, for example MS, in particular, a potentially useful candidate for the treatment of the neurodegenerative phase of demyelinating diseases, for example MS.

On the other hand, the glutamate level can also be used for the screening, searching, identification, development and evaluation of the efficacy of compounds for the treatment of demyelinating diseases, for example, MS.

As a consequence, in another aspect, the invention relates to a method for the screening, searching, identification, development and evaluation of the efficacy of compounds for the treatment of demyelinating diseases comprising (i) putting into contact a cell system which produces glutamate with the compound to be assayed and (ii) evaluating the glutamate expression, in such a manner that if the level of glutamate decreases, the assayed compound is a compound potentially useful for the treatment of demyelinating diseases, aid cell system can be practically any cell system (e.g. a cell), which produces glutamate either naturally or by recombination. The production of glutamate can be evaluated by any conventional method, for example, by enzymatic methods using the glutamate dehydrogenase enzyme, as mentioned before. When a compound reduces the production of glutamate, this compound is classified as a potentially useful candidate for the treatment of demyelinating diseases, for example, MS, and in particular, a potentially useful candidate for the treatment of the neurodegenerative phase of demyelinating diseases, for example, MS.

Also, in another aspect, the invention relates to the use of (i) a nucleotide sequence of a gene selected from the EAAT1, EAAT2 and EGF genes, or of (ii) an amino acid sequence of a protein selected from EAAT1, EAAT2 and EGF, or of (iii) an antibody with a capacity to bind to a protein selected from EAAT1, EAAT2 and EGF (or to fragments thereof containing antigenic determinants), in a method of screening, searching, identification, development and evaluation of the efficacy of compounds for the treatment of demyelinating diseases, for example, MS.

In another aspect, the invention relates to an in vitro method for the identification and evaluation of the efficacy of treatments for demyelinating diseases, for example, MS. The method contemplates the quantification of the glutamate levels and the EAAT1, EAAT2 and/or EGF proteins levels or of the expression levels of the EAAT1, EAAT2 and/or EGF genes in a given subject during the distinct phases or stages of the disease, or during the periods of treatment and absence thereof, and its comparison with control values considered normal values or with previous values from the same patient. When an agent reduces the glutamate levels or increases the expression of EAAT1, EAAT2 or EGF, this agent is considered a candidate for the treatment of demyelinating diseases, and in particular, a candidate for the treatment of the neurodegenerative phase of demyelinating diseases, for example, MS.

Compounds which block the inhibition of the expression or the activity of a glutamate transporter selected from the EAAT1 and EAAT2 transporters, as well as compounds which promote or enhance the expression of the EAAT1 and/or EAAT2 transporters, and compounds which reduce the glutamate levels can be employed in the treatment of demyelinating diseases, for example, MS, and in particular, in the treatment of the neurodegenerative phase of said diseases. By way of non-exclusive illustration, said compounds include cytotoxic agents, chemotherapeutic agents including organic and inorganic molecules, peptides, phosphopeptides, antibiotics and growth factors which promote the expression of the EAAT1 and/or EAAT2 transporters, that is, positive modulators of the expression of the said transporters, for example, EGF.

In another aspect, the invention relates to a pharmaceutical composition comprising a therapeutically effective quantity of a compound which blocks the inhibition of the expression or activity of a glutamate transporter, selected from the EAAT1 and EAAT2 transporters, or of a compound which promotes or enhances the expression of said EAAT1 and/or EAAT2 transporters, or of a compound which reduces the glutamate level, together with one or more pharmaceutically acceptable excipients and/or vehicles. Non-exclusive examples of said compounds which block the inhibition of the expression or the activity of the EAAT1 and/or EAAT2 transporters, or of compounds which promote or enhance the expression of said EAAT1 and/or EAAT2 transporters, or of compounds which decrease the glutamate levels, include cytotoxic agents, chemotherapeutic agents, including organic or inorganic molecules, peptides, phosphopeptides, antibiotics and growth factors which promote the expression of the EAAT1 and/or EAAT2 transporters. In a particular embodiment, said pharmaceutical composition comprises a positive modulator of the expression of the said transporters, for example, EGF.

The excipients, vehicles and auxiliary substances must be pharmaceutically and pharmacologically tolerable and they have to be combinable with other components of the formulation or preparation and not exert any adverse effect on the treated subject. The pharmaceutical compositions can take any form which is appropriate for administration, for example, pharmaceutically adequate forms for oral and parenteral administration (including, e.g. intravenous, subcutaneous, intradermal, intramuscular, intraperitoneal and intrathecal administration). The formulations can be single dose, and will be prepared in accordance with the classical Galenic methods. A review of the distinct pharmaceutical forms of administration and their preparations can be found in the book "Tratado de Farmacia Galénica" by C. Faulí i Trillo, 10th Edition, 1993, Luzán 5, S.A. Editions.

In another aspect, the invention relates to the use of a compound which blocks the inhibition of the expression or the activity of a glutamate transporter selected from the EAAT1 and EAAT2 transporters, or of a compound which promotes the expression of said EAAST1 and/or EAAT2 transporters, or of a compound which reduces the glutamate level, in the manufacture of a pharmaceutical composition for the treatment of demyelinating diseases, for example, MS, in particular, for the manufacture of a pharmaceutical composition for the treatment of the neurodegenerative phase of said demyelinating disease.

In another aspect, the present invention relates to a kit useful to put into practice the methodology herein described. Thus, said kit can contain the necessary reagents for the detection of the glutamate levels, or for the detection of the expression levels of the mRNAs expressing EAAT1, EAAT2 or EGF, or their corresponding cDNA, among which are included:
- a) the glutamate dehydrogenase enzyme (for the detection of glutamate); and/or
- b) one or more antibodies with a capacity to bind to a protein selected from EAAT1, EAAT2 and EGF, or to fragments thereof which contain antigenic determinants; and/or
- c) one or more oligonucleotide primer pairs capable of specifically amplifying a fragment of the mRNA or cDNA encoding EAAT1, EAAT2 and EGF.

The kit of the invention can be used to detect a demyelinating disease in a subject, or to determine the status or severity of said disease in a subject, or to monitor the effect of the administered therapy to a subject showing said.

The following example illustrates the invention, although it must not be considered limiting thereof.

EXAMPLE 1

I. Experimental Procedures

Oligodendrocyte Cultures

Cell cultures were prepared from 12 days-old rat optic nerve following standard protocols, which have been adapted and introduced into the laboratory as recently reported (Matute et al., 1997, Proc. Natl. Acad. Sci. USA 94: 8830-8835).

In Vitro Electrophysiological Recording of Oligodendrocytes

Electrophysiological recordings were carried out on 2 to 5 days-old cultures, following previously published protocols (Patneau et al., 1994, Neuron 12, 357-371). Cells were registered in a chamber which allows changing the composition of the extracellular medium by means of constant flow (0.5 to 1 ml/minute). Registering electrodes used were glass capillaries containing specific solutions compatible with cytoplasmic ionic concentrations. The study of the responses mediated by the glutamate transporters was carried out using whole cell patch clamp.

Experiments Using Isolated Optic Nerve

Nerves were isolated from young adult rats and were perfused for 30 minutes in artificial cerebrospinal fluid (aCSF) saturated in oxygen by means of bubbling of 95% oxygen and 5% carbon dioxide, under conditions comparable to those disclosed for cultured oligodendrocytes (Fern and Möller, 2000, J. Neurosci. 20: 34-42). Next, they were incubated with transporter inhibitors for 6 hours with oxygen saturated normal aCSF. Subsequently, damage was evaluated histologically as described in vivo (Matute, 1998, Proc. Natl. Acad. Sci. USA 95:10229-10234) and biochemical changes underlying this damage were analyzed.

Immunochemical Methods For Oligodendrocyte Cultures and Optic Nerves

In order to study the presence of markers of the oligodroglial lineage, components of myelin, astrocytes and microglia, commercial antibodies were used. Techniques included immunocytochemistry, immunohistochemistry and immunoblotting (Western blot), all of which have been described elsewhere (see for example, Domercq et al., 1999, Eur. J. Neurosci. 11: 2226-2236).

Application of Substances to the In Vivo Optic Nerve

Optic nerve experiments were carried out on (New Zealand White) rabbits which, due to their size, facilitate a better experimental surgical manipulation. The procedure used has been reported previously (Matute, 1998, Proc. Natl. Acad. Sci. USA 95: 10229-10234). Oligodeoxynucleotides were applied using osmotic micropumps which liberate small quantities of solute over a given time. Subsequently, the effect of this treatment on the nerve was evaluated using a panel of oligodendrocytes markers and their progenitors, myelin, axon integrity, astrogliosis and microgliosis.

Analysis of Samples of Blood and Post Mortem Human Tissue

The expression of the EAAT1 and EAAT2 glutamate transporters and of the epidermic growth factor (EGF) was analyzed by means of real time quantitative PCR using as marker the SYBRGreen PCR universal master mix reagent (Applied Biosystems).

The protein levels of EAAT1 and EAAT2 were analyzed by means of immunohistochemistry and conventional Western blot (Domercq et al., 1999, Eur. J. Neurosci 11: 2226-2236). The functional nature of the transporters was determined by tritiated glutamate uptake assays using glial membrane vesicular preparations, in accordance with previously reported methodology (Nakamura et al., 1993, Glia 9: 48-56). The glutamate levels in plasma were determined using an enzymatic assay based on the activity of the glutamate dehydrogenase enzyme (Veis et al., 1998, Nature 391: 281-285).

II) Results

Expression of Functional Glutamate Receptors in Oligodendrocytes

In order to demonstrate the expression of functional glutamate transporters, electrophysiological readings of oligodendrocytes with voltage clamp at −70 mV were performed. The application of glutamate induced a rapid, desensitizing current due to the activation of glutamatergic receptors. Said current is followed by a permanent, non-desensitizing current (mean amplitude=16.54±1.66 pA; n=46; FIG. 1A,B). Said current is sensitive to the substitution of extracellular sodium for lithium, demonstrating that it is due to the activation of sodium-dependent transporters (n=5; FIG. 1A,B). Said currents are also activated by aspartate, substrate of the transporter (mean amplitude=14.26±2.41 pA; n=12; FIG. 1B,C). Finally, currents induced by glutamate or aspartate were inhibited in the presence of DL-threo-β-benzyloxyaspartate (TBOA; 1 mM; FIG. 1D), which is a competitive inhibitor of the GLAST and GLT-1 glutamate transporters (Shimamoto et al., 1998, Mol. Pharmacol. 53: 195-201).

In order to characterize the subtype of transporter, tritiated glutamate uptake assays and immunocytochemistry were used. The sodium-dependent uptake of glutamate in oligodendrocytes was totally inhibited in the presence of TBOA (n=3; FIG. 1E). In contrast, dihydrokainate (DHK), which is a selective inhibitor of GLT-1, only partially inhibited glutamate uptake (n=4; FIG. 1E), indicating that both GLAST and GLT-1 subtypes are functional in oligodendrocytes. Accordingly, both subtypes were detected in in vitro oligodendrocytes by means of immunocytochemical assays (FIG. 1F).

Inhibition of Glutamate Transporters Produces Oligodendroglial Death

Figure 2:
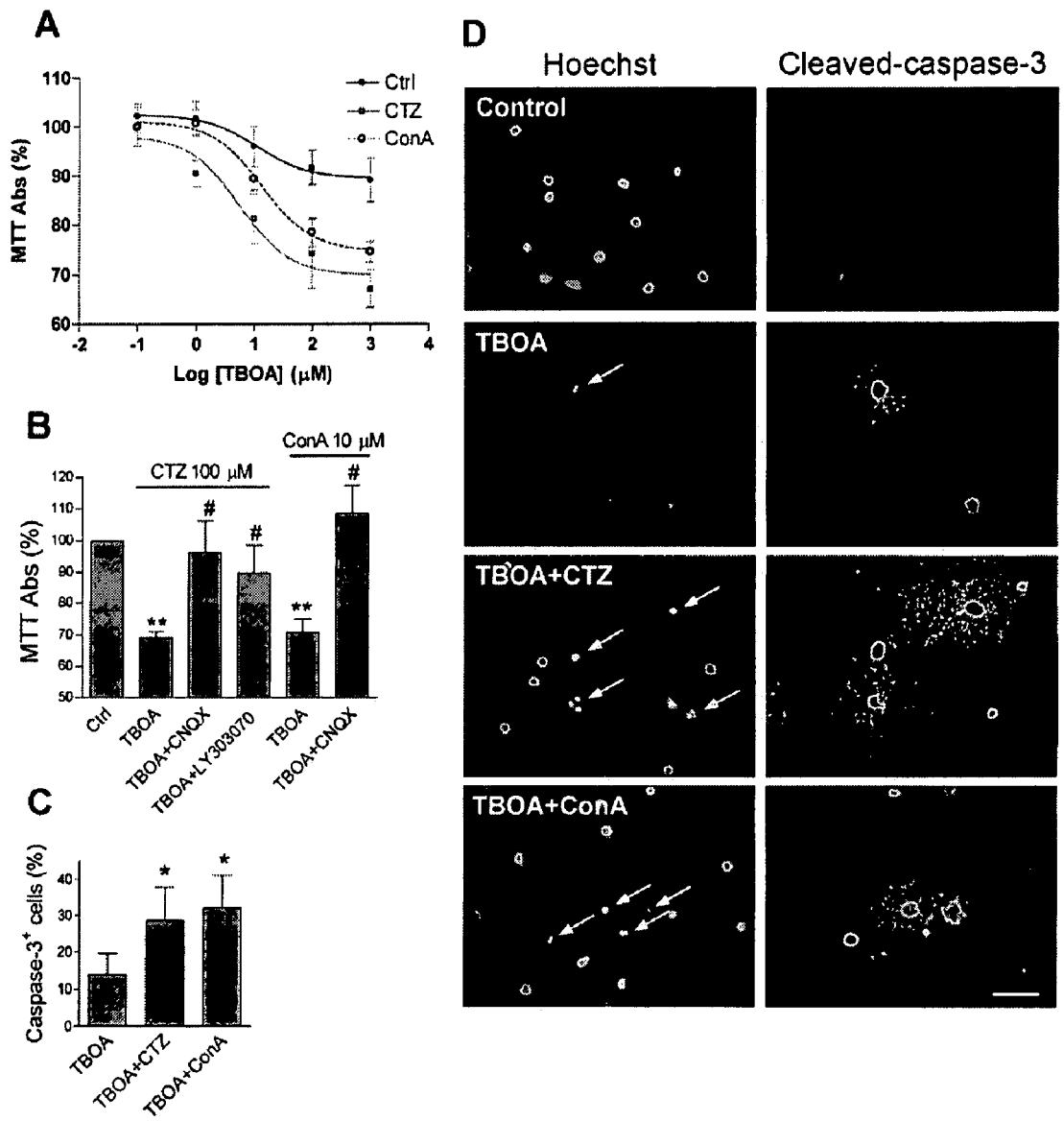
FIG. 2 shows that the inhibition of glutamate transporters leads to oligodendroglial death in vitro. Death is produced due to the activation of AMPA/kainate receptors since it is enhanced in the presence of cyclothiazide and concanavalin A, which are inhibitors of the desensitization of AMPA and kainate receptors respectively, and it is blocked in the presence of CNQX, an antagonist of AMPA/kainate receptors.

Inhibition of glutamate transporters with TBOA (100 nM to 1 mM; 24 h) produces oligodendroglial death ($EC_{50}$=10.9 µM; n=5), which is maximal at concentration 1 mM of the inhibitor (FIG. 2A). This TBOA-induced oligodendroglial death is enhanced in the presence of cyclothiazide (CTZ; 100 µM) and concanavalin A (ConA; 10 µM), which are inhibitors of the desensitization of AMPA and kainate receptors respectively ($EC_{50}$=5.5 µM and 13.6 µM respectively; n=3-5; FIG. 2A). TBOA-induced death is blocked in the presence of 6-cyano-7-nitroquinoxalin-2,3-dione (CNQX; 30 µM), which is an antagonist of AMPA and kainate receptors and is reduced to a large extent in the presence of LY303070 (50 µM), which is an antagonist of AMPA receptors (n=3; FIG. 2B), indicating that glutamate receptors are implicated in the death induced by the inhibition of glutamate transporters. TBOA alone or in the presence of CTZ (100 µM) or ConA (10 µM) produces chromatin condensation and activation of caspase-3 in dying oligodendrocytes (FIG. 2C,D), indicating that these cells die by apoptosis.

Figure 3:
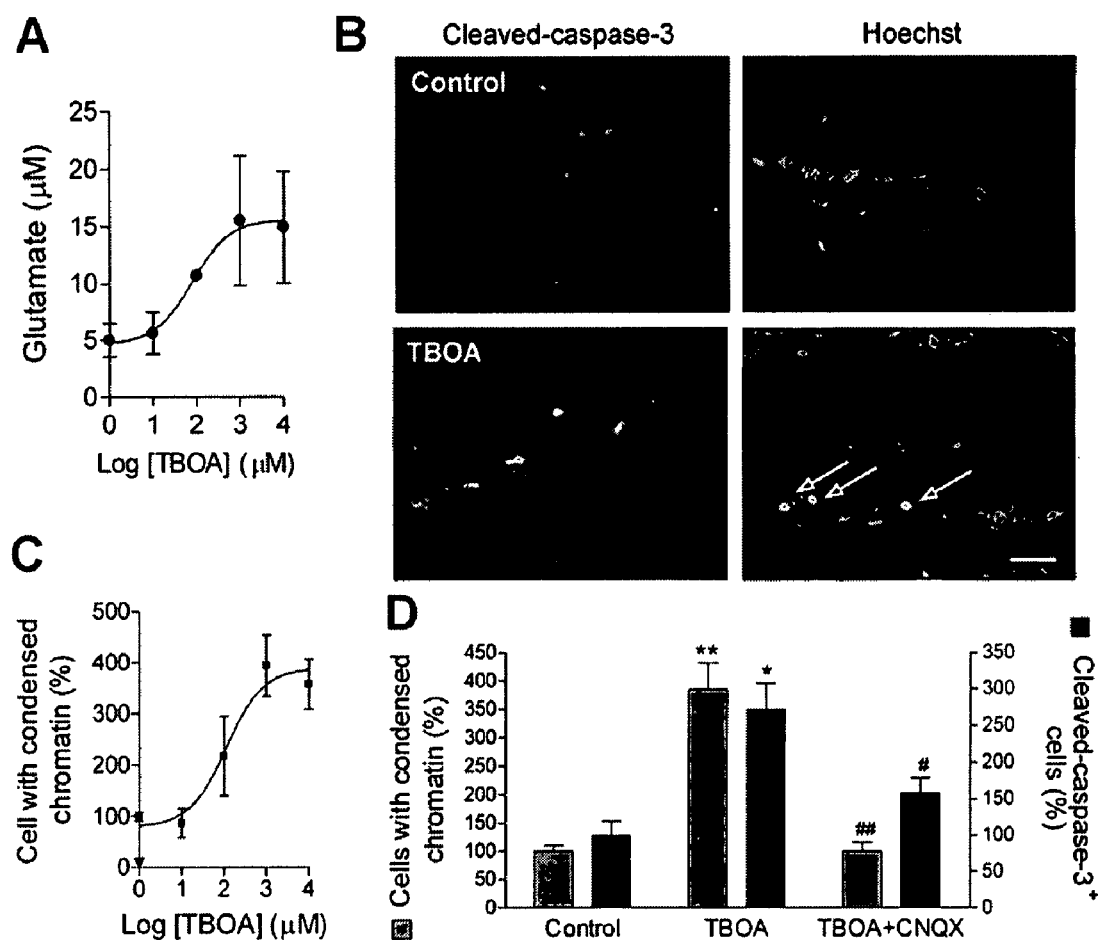
FIG. 3 shows that the inhibition of glutamate transporters in in situ optic nerves gives rise to alterations in glutamate homeostasis which lead to oligodendroglial death mediated by the overactivation of AMPA/kainate receptors.

Inhibition of Glutamate Transporters Kills Oligodendrocytes Both In Situ and In Vivo In order to determine if the inhibition of glutamate transporters is toxic for oligodendrocytes in a preparation of in situ nervous tissue, whole optic nerves isolated from adult rats were perfused with TBOA in aCSF for 6 hours. Under these conditions, the extracellular levels of glutamate are increased to doubled at the maximal concentration of TBOA ($EC_{50}$=78.2 µM; n=3-5; FIG. 3A).

Altered homeostasis produced by TBOA gave rise to more than a 3 fold increase in the number of cells showing chromatin condensation (seen using the Hoechst marker; FIG. 3B) and activation of caspase-3 in comparison to control nerves ($EC_{50}$=113.2 µM; n=6-12; FIG. 3B, C, D). Damaged cells are oriented along the longitudinal axis of the nerve and are part of interfascicular oligodendrocyte rows (FIG. 3B). Incubation with TBOA in the presence of CNQX (30 µM) prevents oligodendrocyte death (FIG. 3D).

Figure 4:
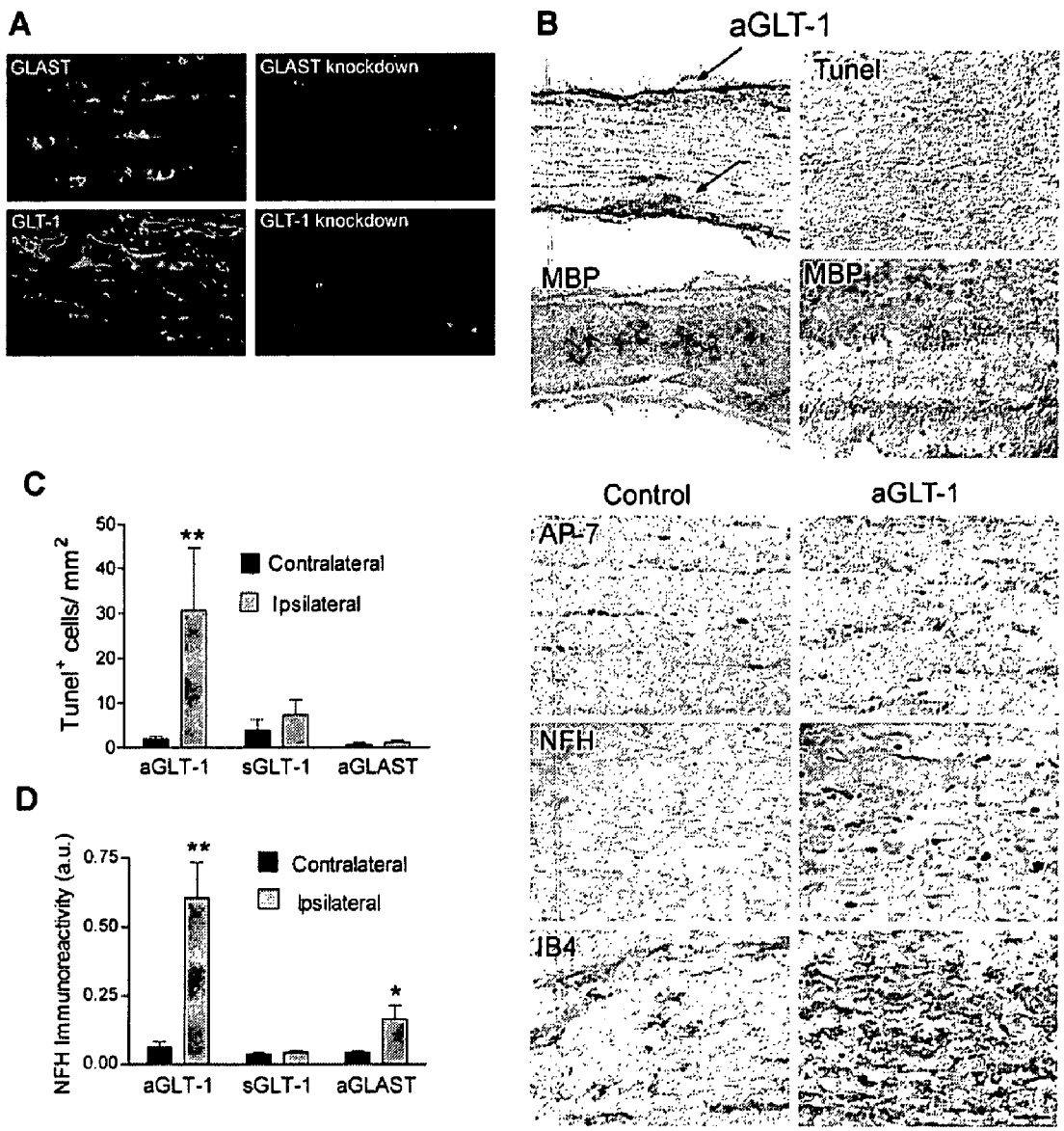
FIG. 4 illustrates how the slow infusion (1 μl/hour; 3 days) of oligonucleotides which are antisense to the GLT-1 transporter (1 μM) causes lesions in the optic nerve, in which tissue damage and microgliosis can be observed, as well as the disappearance of myelin in the damaged area and the disruption of axons.

Next, antisense oligodeoxyribonucleotides (ODNs) specific for the GLAST and GLT-1 transporter subtypes (aGLAST and aGLT-1 respectively) were infused into the optic nerve of rabbits in vivo by means of osmotic pumps which liberate small quantities of solute over 3 days, analyzing after 7 days its effects via immunohistochemical techniques. Said antisense oligonucleotides reduced in an efficient manner the expression of the GLAST and GLT-1 transporters in the rabbit optic nerve, as can be seen from the immunohistochemical analysis (FIG. 4A). The application of antisense ODNs against GLT-1 induced severe tissue damage and oligodendroglial death (FIG. 4B). Moreover, said zone shows intense gliosis, lack of myelin and axon damage (FIG. 4B, C, D). In contrast, the application of antisense ODNs against aGLAST produce lesions in more restricted areas mainly characterized by axon damage (FIG. 4D). Finally, the administration of sense ODNs against GLT-1 (sGLT-1), used as control, did not produce any alteration to the optic nerves (FIG. 4C,D). Together, these results indicate that the inhibition of glutamate transporters causes the death of oligodendrocytes in situ and that the in vivo lesions share properties characteristic of MS plaques, such as local inflammation and demyelination.

Analysis of the Expression of EAAT1, 2 and 3 in Control and MS Optic Nerves

Figure 5:
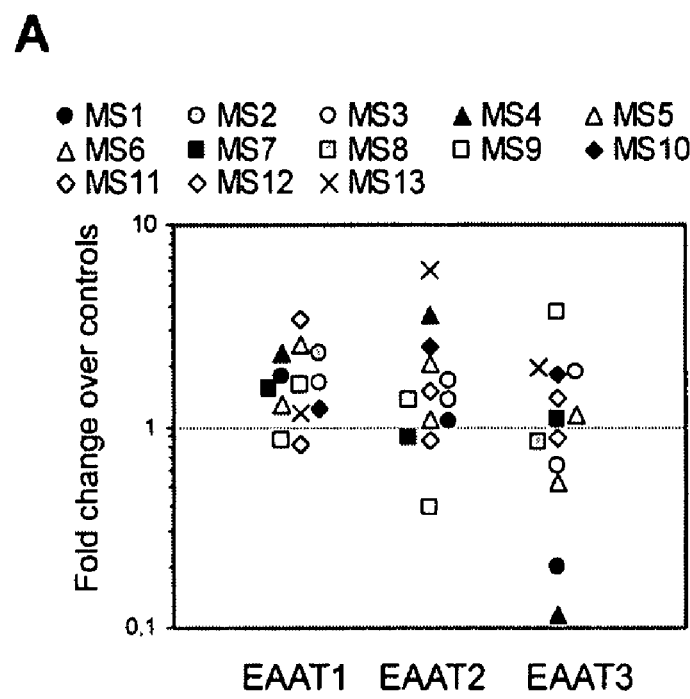
FIG. 5 shows that the levels of RNA encoding EAAT1 and EAAT2 are elevated in the optic nerve of MS patients.
Figure 5:
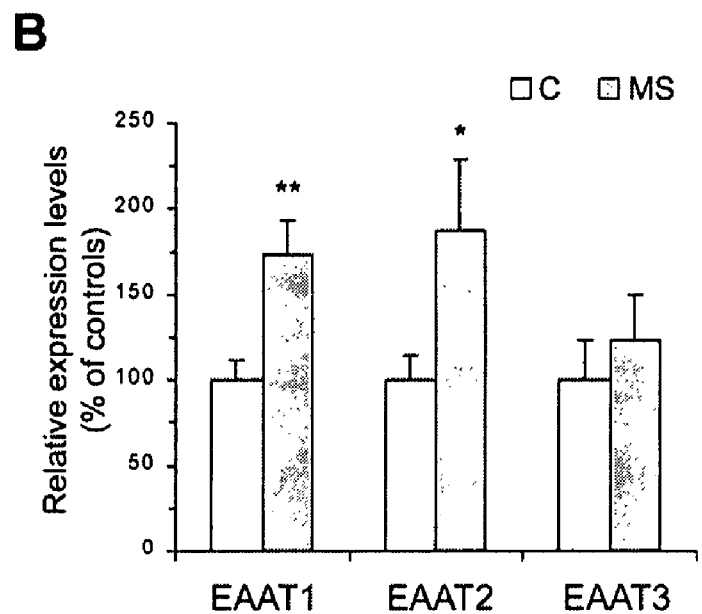

Using quantitative PCR, the expression of the EAAT1, EAAT2 and EAAT3 transcripts was analyzed in samples from control subjects and MS patients. The levels of the EAAT1 and EAAT2 transporters are increased in MS with respect to controls. These increases were found in 11 of the 13 samples analyzed for the EAAT1 subtype (mean increase=1.75; $p<0.005$; FIGS. 5A and B). In contrast, the expression of EAAT2 was more variable with increases in 8 samples, absence of changes in 4 and decrease in one case (FIG. 5A), seeing in its entirety significant increases in EAAT2 expression in MS patients (mean increase=1.87; $p<0.05$; FIG. 5B). Finally, there is no change in EAAT3 levels in the analyzed MS samples (FIG. 5B).

Figure 6:
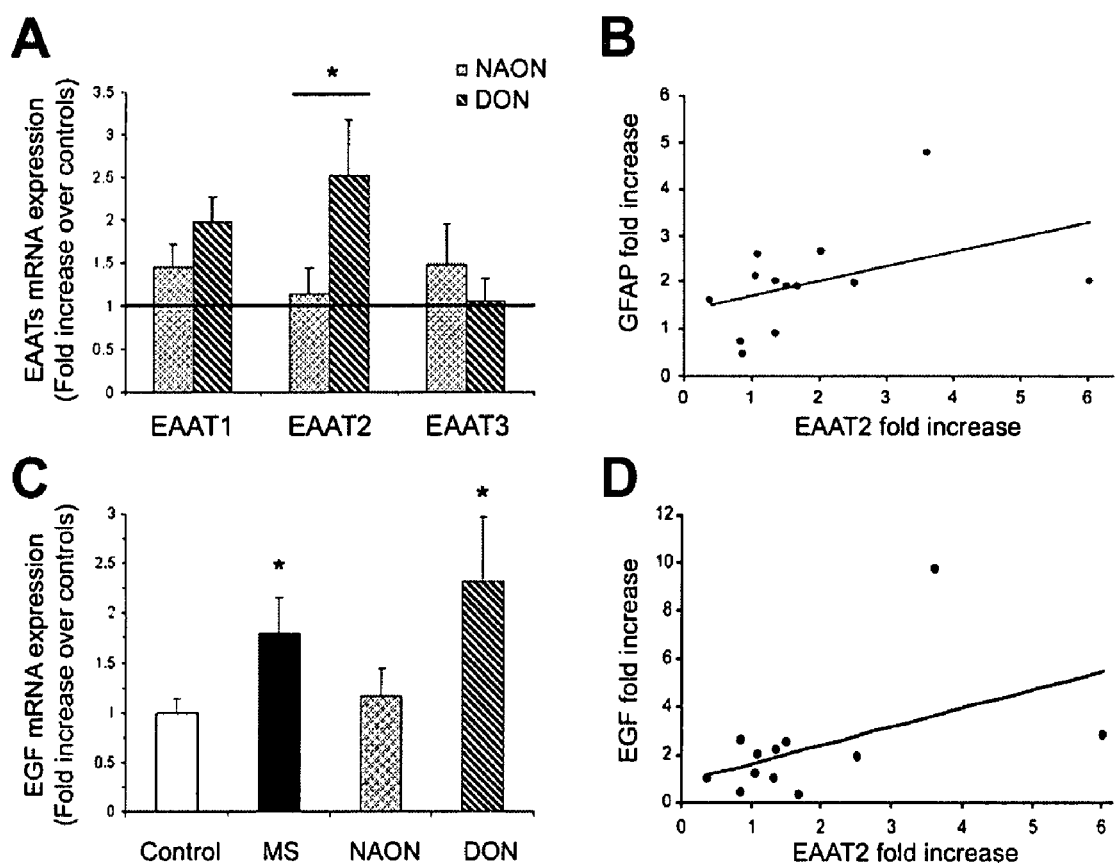
FIG. 6 shows that the levels of EAAT2 are elevated only in optic nerves with visual alterations, such as optic neuritis, and that the expression of EAAT2 is correlated with EGF, positive modulator of its transcription.

Next, it was analized if the expression levels of the EAAT transporters bore any correlation with clinical or pathological data from each patient. No correlation was found between the different subtypes of MS and the expression levels of EAAT1 and EAAT2. However, the expression of EAAT2 is higher in optic nerves showing visual alterations in comparison to normal appearing nerves (2.5 fold more; $p<0.05$; FIG. 6A). In addition, the expression of EAAT2 was correlated with the GFAP levels (r=0.56; FIG. 6B) and with EGF (r=0.455; FIG. 6D), which is a potent positive modulator of the transcription of EAATs (Su et al., 2003, Proc. Natl. Acad. Sci. USA 100: 1955-1960; Kim et al., 2003, J. Neurochem. 87: 1485-1498). These findings indicate that the EAAT2 transporter is overexpressed in astrocytes due to the action of the positive modulator EGF.

Figure 7:
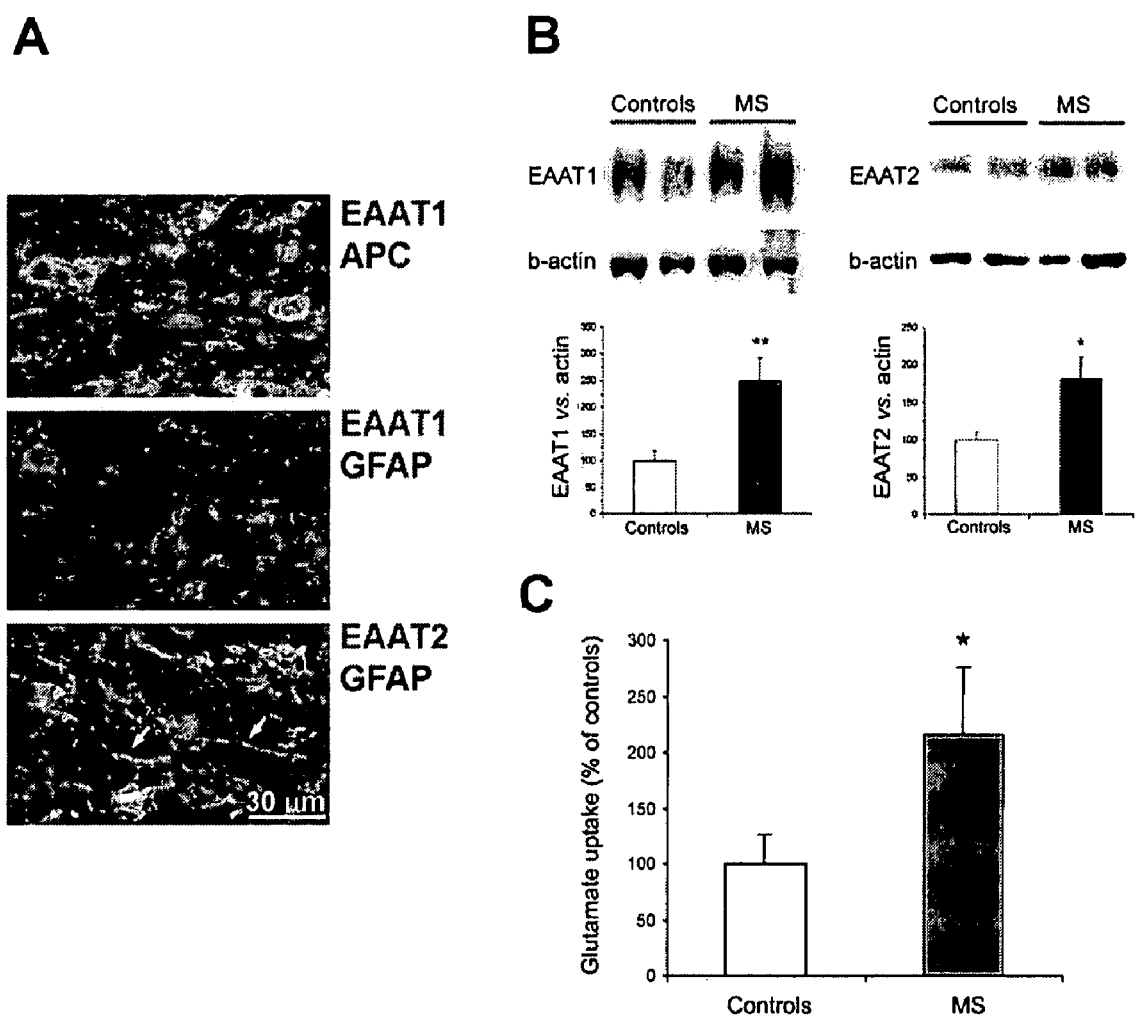
FIG. 7 shows the in situ expression of glutamate transporters in post-mortem human optic nerve. It is shown that the protein levels of the EAAT1 and EAAT2 as well as the functioning thereof are elevated in optic nerve from MS patients.

In order to evaluate changes at the protein level, conventional techniques were used such us Western blot and immunohistochemistry. The distribution of EAAT1 and EAAT2 transporters in human optic nerve is similar to that observed in white matter tracts from rat (Domercq et al., 1999, Eur. J. Neurosci. 11: 2226-2236). Thus, EAAT1 transporter is localized in oligodendrocytes labeled with adenomatous polyposis sporadic colorectal cancer (APC), while EAAT2 is distributed in GFAP positive astrocyte processes (FIG. 7A). In optic nerves from MS patients appear an increase in the immunoreactivity, but not detecting changes in the expression pattern. Similarly, Western blot analysis shows that the protein levels of EAAT1 and EAAT2 are increased significantly in protein homogenates from MS optic nerves (n=13; $p<0.05$; FIG. 7B). To evaluate the relevance of these protein changes, functional glutamate uptake assays using glial membrane vesicular preparations (GPVs) from human optic nerves were carried out. The capacity of sodium-dependent transport of the GPVs in the human optic nerve is low with respect to other regions 12.4 pmol/mg prot/min. However, glutamate uptake in GPVs of samples from MS patients is significantly increased with respect to control samples (n=6; $p<0.05$; FIG. 7C).

Figure 8:
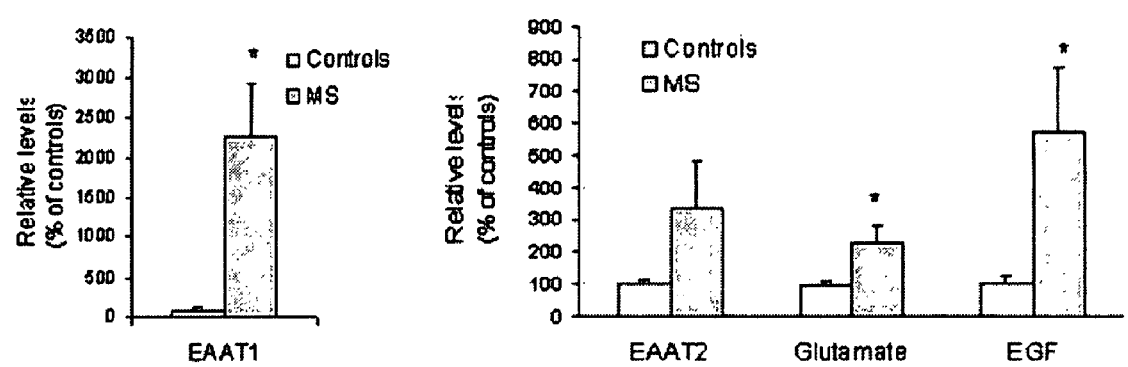
FIG. 8 shows that the levels of glutamate as well as EAAT1 and EAAT2 levels are elevated at peripheral level, in samples of blood from MS patients. Said increases are due to the effect of the EGF positive modulator which is also increased in said samples.

Expression and Modulation of the Transporters in Blood From Control Subjects and MS Patients The expression levels of transporters could be a reflect of the increase of glutamate levels in blood and may be related to the clinical status of the patient. For this reason, the expression of transporters as well as the level of plasma glutamate in control subjects and MS patients was analyzed. The concentration of glutamate in blood was elevated in MS patients with respect to control subjects (n=35; FIG. 8). Paralleling to said increase, MS patients show increases in the expression of EAAT1 and EAAT2 transporters (n=20 and 39 respectively; FIG. 8). In addition, the expression of the positive modulator EGF was found to be elevated, as occurs in the optic nerve, whereas increases in the levels of TNFα were not found, a negative modulator of the expression of these transporters (n=22; FIG. 8).

Figure 9:
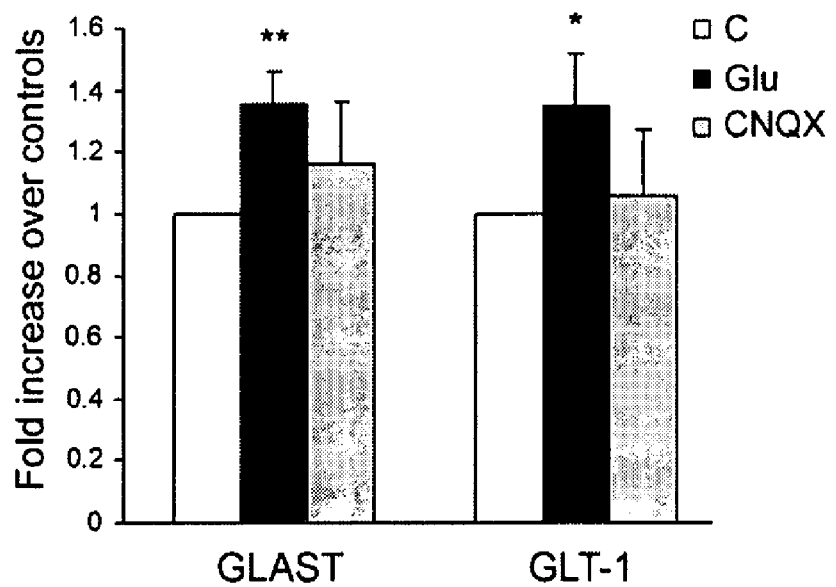
FIG. 9 shows that in situ excitation of the optic nerve with glutamate is sufficient to induce an increase in the expression of EAAT1 (GLAST) and EAAT2 (GLT-1) transporters and that such increases are accompanied by increases in the EGF positive modulator.
Figure 9:
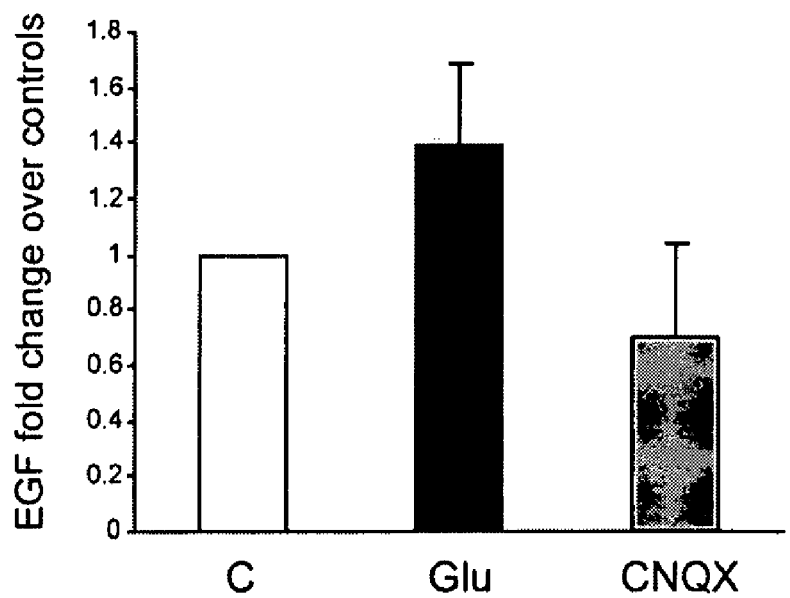

Finally, in order to demonstrate that EAAT overexpression observed in the blood and optic nerve of MS patients is due to an alteration in the levels of glutamate, the response of the isolated optic nerve preparation to stimulation with high levels of glutamate was analyzed. After 3 hours of incubation with glutamate (1 mM), an increase in the expression of the EAAT1 and EAAT2 transporters and of the EGF positive modulator is induced (n=5; FIG. 9). Thus, it can be conclude that the alteration in the glutamate levels in MS causes transporters overexpression of said amino acid, in order to compensate the toxic effects thereof and that said overexpression is principally mediated by EGF, a positive modulator of the EGF transcription.

III. Discussion

The present results demonstrate that oligodendrocytes and white matter tracts have glutamate transporters. Also, the electrophysiological, pharmacological and molecular properties of these transporters are described in detail, as well as the effects which inhibition of the same has on said cells or tracts. The blockade of the transporters is toxic for oligodendrocytes and induces tissue damage and demyelination due to the overactivation of glutamatergic receptors which resembles lesions observed in MS. Thus, mechanisms direct to enhance the expression of these transporters may produce benefits to prevent oligodendroglial death and axon damage.

Glutamate transporters can be blocked by oxidative stress as well as by proinflammatory cytokines such as TNFα, which would give rise to changes in glutamate concentration. However, the transporters present a mechanism of dinamic regulation to increase their expression when a change in the glutamate homeostasis occurs. Given that glutamate levels are increased in MS patients, an increase in the expression of the EAAT1 and EAAT2 transporters occurs in said pathology in order to try to recuperate normal glutamate levels and thus minimize damage. EGF is the most potent positive modulator of the expression of the EAAT1 and 2 transporters whose expression is found to be elevated in blood as well as in optic nerve, indicating that it may well be an ideal therapeutic tool to prevent excitotoxicity in said disease.

The invention described herein constitutes, in first place, a diagnostic marker for MS which permits the establishment of a correlation between the clinical status of the patient with a variable such as the level of glutamate or the expression of EAAT1 and EAAT2 transporters and of EGF factor. Biological markers in body fluids such as cerebrospinal fluid and blood, can provide an objective biological indicator of the prognosis of the patient and provide more information to the patient regarding future episodes. For MS, there are various types of markers of inflammatory activity, however there are no markers of axon damage or of the neurodegenerative phase of the disease (Teunissen et al., 2005, Lancet 4: 32-41). Glutamate has been related to the neurodegenerative phase since it induces oligodendroglial death (Matute et al., 1997, Proc. Natl. Acad. Sci. USA 94: 8830-8835) and its levels are elevated in the cerebrospinal fluid of MS patients (Stover et al., 1997, Euro. J. Clin. Invest. 27: 1038-1043; Sarchielli et al., 2003, Arch. Neurol. 60: 1082-1088). However, the origin of glutamate homeostasis change in EM is still unknown. One possibility is that the increases within the CNS are due to an alteration of the blood-brain barrier, as a consequence of immune attack. This perturbation would facilitate the entrance of glutamate from the blood system to the brain, given the existence of a positive gradient (Westergren et al., 1994, J. Neurochem 62, 159-165). Thus, the monitoring of molecules implicated in glutamatergic signaling, such as glutamate and its transporters in blood constitutes a potential marker for the prognosis and for the study of demyelinating diseases. A preferential embodiment of the invention consists of the use of said parameters as markers of MS.

On the other hand, these parameters are the basis for a wide range of novel therapeutic strategies based on the regulation of glutamate transporters in demyelinating diseases, and in particular in MS, a disease which has no effective treatment to slow or impede its progression. Therapeutic strategies based on drugs which are currently employed for the treatment of MS, or are in clinical assay phases have mechanisms of action which regulate the functioning of the immune system. However, the proposed strategy, upon preventing the alteration of glutamate homeostasis has a larger therapeutic potential for the neurodegenerative phase of this disease, which can last for many tens of years, and in which patients suffer a progressive deterioration involving motor and sensory perturbations which eventually lead to invalidity.

On the other hand, positive modulators of the transcription of glutamate transporters, such as molecules which signal via the EGF receptor route, including EGF, act by reducing the extracellular concentration of glutamate and thus prevent cell damage. This may constitute an endogenous defense mechanism, which contributes to the restoration of equilibrium in the face of any stimulus or assault which produces alterations in glutamate levels. Thus, the invention contemplates the enhancement of these defense mechanisms via the external contribution of factors which enhance the expression of EAAT1 and EAAT2 as well as EGF.

The invention claimed is:

1. An in vitro method, to detect a demyelinating disease in a subject, or to determine the status or severity of said disease in a subject, or to monitor the effect of a therapy administered to a subject who presents said disease, said method comprising conducting a procedure selected from among Procedure A and Procedure B, wherein the procedure is conducted on a sample of the subject selected from among samples of blood, serum, plasma, urine, saliva, excrement, cerebrospinal fluid and peritoneal liquid, wherein Procedure A comprises:
  a) quantifying the level of expression of a nucleic acid in the sample from said subject, wherein said nucleic acid is selected from the nucleic acid encoding the subtype 1 glutamate transporter (EAAT1), the nucleic acid encoding the subtype 2 glutamate transporter (EAAT2), and the nucleic acid encoding the epidermal growth factor (EGF), and any combination thereof; and
  b) comparing said level with that from a control sample; wherein an increment in said level with respect to the level in the control sample indicates the presence of a demyelinating disease;

and wherein Procedure B comprises:
  a) quantifying the protein level in the sample from said subject, wherein said protein is selected from the subtype 1 glutamate transporter (EAAT1), the subtype 2 glutamate transporter (EAAT2), the epidermal growth factor (EGF), and any combination thereof; and
  b) comparing said level with that from a control sample; wherein an increment in said level with respect to the level in the control sample indicates the presence of a demyelinating disease.

2. The method according to claim 1, wherein said demyelinating disease is selected from among multiple sclerosis (MS), Devic's syndrome, Baló's disease, Marchiafava-Bignami disease, central pontine myelinolysis, acute disseminated encephalomyelitis and acute necrotizing hemorrhaging encephalomyelitis.

3. The method according to claim 1, comprising subjecting said sample to a process of extraction to obtain an extract comprising total RNA, protein extract, plasma or serum.

4. The method according to claim 1, wherein said sample is obtained from a subject who has not been previously diagnosed with a demyelinating disease, or from a subject who has been previously diagnosed with a demyelinating disease, or from a subject who is receiving treatment for a demyelinating disease, or from a subject who has received treatment for a demyelinating disease.

5. The method according to claim 1, comprising quantifying the level of mRNA or cDNA encoding EAAT1, the level of mRNA or cDNA encoding EAAT2 and/or the level of mRNA or cDNA encoding EGF.

6. The method according to claim 5, wherein the quantification of the levels of said mRNA or the corresponding cDNA comprises amplifying the mRNA or the corresponding cDNA synthesized by reverse transcription of the mRNA and a step of quantifying the amplification product from said mRNA or cDNA.

7. The method according to claim 6, wherein said amplification is carried out qualitatively or quantitatively by means of PCR using oligonucleotide primers which specifically amplify a nucleic acid encoding the EAAT1, EAAT2 or EGF.

8. The method according to claim 7, wherein the quantification of the level of mRNA expressing EAAT1, the level of mRNA expressing EAAT2 or the level of mRNA expressing EGF is carried out by means of real time quantitative PCR.

9. The method according to claim 1, comprising quantifying the level of a protein selected from EAAT1, EAAT2, EGF and any combinations thereof.

10. The method according to claim 9 wherein the quantification of the level of the EAAT1, EAAT2 or EGF protein is performed by means of antibodies that bind to said proteins, or to fragments thereof which are specific to said proteins and can elicit an antibody specific to said proteins, determinants and using immunochemical techniques to quantify antigen-antibody binding.

11. An in vitro method for the identification and evaluation of the efficacy of treatments for demyelinating diseases, comprising quantifying the levels of EAAT1 and/or EGF proteins, or quantifying the expression levels of the nucleic acids encoding EAAT1 and/or EGF in a sample of a given subject during distinct phases or stages of the disease, or during the periods of treatment and/or absence thereof, and comparing said levels with control values considered to be normal or with values obtained previously from a same subject, wherein the sample of the subject is selected from among samples of blood, serum, plasma, urine, saliva, excrement, cerebrospinal fluid and peritoneal liquid, and wherein an increase in levels determined by said quantifying is indicative of a worsening of said disease in said patient, and wherein a decrease in levels determined by said quantifying is indicative of improvement of said patient having said disease.

* * * * *

UNITED STATES PATENT AND TRADEMARK OFFICE
CERTIFICATE OF CORRECTION

Page 1 of 1

PATENT NO.         : 7,879,568 B2
APPLICATION NO.    : 11/915324
DATED              : February 1, 2011
INVENTOR(S)        : Carlos Matute Almau It is certified that error appears in the above-identified patent and that said Letters Patent is hereby corrected as shown below:

Column 19, lines 16-17 (claim 6): "levels of said mRNA or the corresponding cDNA comprises amplifying the mRNA or the corresponding cDNA" should be -- levels of said mRNA or the cDNA comprises amplifying the mRNA or the cDNA --.

Column 20, lines 9-10 (claim 10): "can elicit an antibody specific to said proteins, determinants and using immunochemical techniques" should be -- can elicit an antibody specific to said proteins, and using immunochemical techniques --.

Signed and Sealed this
Sixteenth Day of August, 2011

David J. Kappos
*Director of the United States Patent and Trademark Office*